United States Patent [19]

Nakano

[11] Patent Number: 5,814,319
[45] Date of Patent: Sep. 29, 1998

[54] ANTI-VIRAL, ANTI-BACTERIAL AND ANTI-CANCER AGENT

[75] Inventor: Masatoshi Nakano, Chiryu, Japan

[73] Assignee: Mitsui Norin Co., Ltd., Tokyo, Japan

[21] Appl. No.: 621,825

[22] Filed: Mar. 22, 1996

[51] Int. Cl.⁶ .................................................. A01N 65/00
[52] U.S. Cl. ....................... 424/195.1; 424/686; 424/688; 514/932; 514/933; 514/934
[58] Field of Search .................. 424/195.1, 686, 424/688; 514/932, 933, 934

[56] References Cited

U.S. PATENT DOCUMENTS 5,525,340   6/1996   Fukunaga ............................. 424/195.1

OTHER PUBLICATIONS

Database WPI, Week 9516, Derwent Publications Ltd., London, GB, Feb. 10, 1995, AN 95–117827, of JP–A–07–039 339 (Ruibosuti Japan KK), 10 Feb. 1995;.
Yoshimi Kujiyou, "Production of Rooibos Tea Extract Excellent in Color, Tone and Taste", Patent Abstracts of Japan of JP–A–07 039 339, Feb. 10, 1995;.
Database WPI, Week 9346, Derwent Publications Ltd., London, GB, Oct. 19, 1993, AN 93–365133, of JP–A–05 271 062 (Kato K. et al), 19 Oct. 1993;.
Kato et al., "Antiviral, Antibacterial and Fungicidal Agent", Patent Abstracts of Japan of JP–A–05 271 062, Oct. 19, 1993;.
Kato et al., "Carcinostatic Anticancer Agent", Patent Abstracts of Japan of JP–A–05 271 061, Oct. 19, 1993.
Database WPI, Week 9346, Derwent Publications Ltd., London, GB, Oct. 19, 1993, AN 93–365132, of JP–A–05 271 061 (Kato K. et al), 19 Oct. 1993;.
Database WPI, Week 9516, Derwent Publications Ltd., London, GB, Patent Abstract of Japan of JP–A–07 039 339, Feb. 10, 1995, AN 95–117827, of JP–A–07 039 339 (Ruibosuti Japan KK), 10 Feb. 1995;

Patent Abstract of Japan of JP–A–07 039 339, Feb. 10, 1995;.
Database WPI, Week 9346, Derwent Publications Ltd., London, GB, Patent Abstract of Japan of JP–A–05 271 062, Oct. 19, 1993, AN 93–365133, of JP–A–05 271 062 (Kato K. et al.), 19 Oct. 1993;.
Patent Abstracts of Japan of JP–A–05 271 062, Oct. 19, 1993;.
Database WPI, Week 9346, Derwent Publications Ltd., London, GB, Patent Abstrat of Japan of JP–A–05 271 061, Oct. 19, 1993, AN 93–365132, of JP–A–05 271 061 (Kato K. et al), 19 Oct. 1993;.
Patent Abstracts of Japan of JP–A–05 271 061, Oct. 19, 1993.
Kato et al., "Carcinostatic Anticancer Agent" Jul. 19, 1994, Patent Abstracts of Japan, Japanese Patent Office, of JP 04084860.
Kato et al., "Antiviral, Antibacterial and Fungicidal Agent", Jul. 19, 1994, Patent Abstracts of Japan, Japanese Patent Office, of JP 04084861.
Kato et al., "Anti–viral, Anti–bacterial Composition Comprising Substance with Super–Oxide Dismutase and/or Anti–oxide Activity, Glycoprotein and Saccharified Flavonoid", Jul. 19, 1994, Derwent Abstract of JP 6199697, Derwent Publications, Ltd.
Kato et al., "Anti–cancer Agent Comprises Substance Having Superoxide Dismutase Activity", Jul. 19, 1994, Derwent Abstract of JP 619696, Derwent Publications, Ltd.

*Primary Examiner*—Herbert J. Lilling
*Attorney, Agent, or Firm*—Frishauf, Holtz, Goodman, Langer & Chick, P.C.

[57] ABSTRACT

An anti-viral, anti-bacterial, and anti-cancer agent comprising as the effective component, an alkali extraction of *Aspalathus linearis* which is preferably obtained after extraction by hot water. The agent serves to treat and prevent bacterial infections; to treat and prevent cancer; and to treat or prevent viral infection, for example, infection caused by retroviruses, such as human T-cell leukemia and the AIDS virus. The agent has no side effects.

5 Claims, No Drawings

ANTI-VIRAL, ANTI-BACTERIAL AND ANTI-CANCER AGENT

BACKGROUND OF THE INVENTION

1. Field of the Invention

The present invention relates to an anti-viral, anti-bacterial and anti-cancer agent, containing an alkaline extract of *Aspalathus linearis* belonging to the Leguminosae family, as the effective component.

2. Background Information

Numerous anti-viral and anti-cancer agents were known heretofore.

However such anti-viral agents are effective mainly on bacteria and their effectiveness against viruses, if any, is extremely weak. Moreover antibiotics usually have side effects, which can sometimes be severe and serious.

There are many diseases caused by viruses such as influenza, hepatitis, measles, Japanese encephalitis, human T-cell leukemia, and AIDS. Unfortunately though there are few medications which show a definite effectiveness against these kinds of viral diseases, and in particular there is no medicine which is sufficiently effective against retroviruses which cause human T-cell leukemia or AIDS, without having side effects.

Moreover, there are no anti-viral agents known which can be taken in the daily diet and have a preventative effect without having any side effects.

The search for an effective treatment for AIDS and AIDS-related complex, which has no side effects, has been particularly difficult. There are some medicines with limited effectiveness which over long-term chemotherapy can show severe side effects.

As for anti-cancer agents, anti-cancer agents known heretofore work to destroy not only cancer cells, but can also cause damage to normal cells.

These agents show severe side-effects and it is difficult to use these agents as an oral administration. Thus these medicines are usually used intraveneously. As a result there are several problems with these anti-cancer agents.

Therefore an anti-HIV agent and an anti-cancer agent should have no side effects and a strong effectiveness. As for anti-HIV agents, it has been sought to obtain an agent with no side effects, having an inhibitive action on the adhesion of the virus on cells, a suppressive action on virus replication and an action which activates the immune activity.

SUMMARY OF THE INVENTION

The purpose of the present invention is to resolve the above problems and to provide an anti-viral agent that can be taken orally, which is effective against retroviruses and has a protective action with no side effects; to provide an anti-bacterial agent for preventing or treating bacterial infections, and to provide an anti-cancer agent that can be taken orally, which destroys malignant tumors (cancer) with no side effects.

The present invention concerns a composition for treating a human infected with a virus comprising an anti-viral effective amount of an alkaline extract of *Aspalathus linearis* as an active component together with a pharmaceutically acceptable carrier.

The present invention also concerns a composition for preventing or treating a bacterial infection in a human comprising an anti-bacterial effective amount of an alkaline extract of *Aspalathus linearis* as an active component together with a pharmaceutically acceptable carrier.

The present invention also relates to a composition for treating a human infected with a cancer comprising an anti-cancer effective amount of an alkaline extract of *Aspalathus linearis* as an active component together with a pharmaceutically acceptable carrier.

The present invention is further directed to a method of preventing viral infection or treating a human infected with a virus, such as influenza, hepatitis, measles, encephalitis, human T-cell leukemia and human immunodeficiency virus (HIV), for example HIV-1, by administering to the human an anti-viral effective amount of an alkaline extract of *Aspalathus linearis*, either alone or in admixture with a pharmaceutically acceptable diluent.

The present invention is also directed to a method of preventing or treating a bacterial infection, such as Staphylococcus infection such as methicillin resistant *Staphylococcus aureus* (MRSA), and *Staphylococcus pyrogenes*, *streptococcal* infection, *pneumococcal* infection and *clostridium* infection, such as *botulinus* and *salmonellosis* including *S. enteritidis*, in a human by administering to the human an anti-bacterial effective amount of an alkaline extract of *Aspalathus linearis*, either alone or in admixture with a pharmaceutically acceptable diluent.

Moreover, the present invention involves a method of preventing cancer or treating a human suffering from a cancer such as stomach cancer, malignant epithelial tumor (carcinoma), such as lung cancer, intestinal cancer, renal cancer and hepatoma, and also malignant mesenchymal tumor (sarcoma), such as leukemia and myeloma, by administering to the human an anti-cancer effective amount of an alkaline extract of *Aspalathus linearis*, either alone or in admixture with a pharmaceutically acceptable diluent.

Still further, the present invention concerns a method of producing an anti-viral, anti-bacterial, or anti-cancer agent comprising contacting leaves, stems and/or roots of *Aspalathus linearis* with an alkaline solution of at least one alkaline compound selected from the group consisting of sodium carbonate, sodium bicarbonate, potassium hydroxide, sodium hydroxide, ammonium hydroxide and ammonia, and isolating the resultant extract by filtration.

DETAILED DESCRIPTION OF THE INVENTION

The present inventors undertook extensive research in order to resolve the above problems and discovered that an alkaline extract from the leaves, stems and/or roots of *Aspalathus linearis* has a strong anti-viral and anti-cancer action, and that the said alkaline extract is extremely safe and has no side-effects on animals or humans, and thus the present invention was developed.

The effective component of the present invention is derived from an alkaline extract of the leaves, stems, and/or roots of *Aspalathus linearis;* or more desirably the leaves, stems and/or roots are extracted in hot water, and followed by extraction with an alkaline solution.

In the hot water extraction process, the amount of water should be 5 to 1000 fold the weight of *Aspalathus linearis*, and extracted at 70°–100° C. for 5 minutes-10 hours. After extraction with hot water, *Aspalathus linearis* should be dried in the sun or inside for 1–3 days.

To the hot water extraction of the leaves, stems, and/or roots of *Aspalathus linearis* 0.05–5 wt. % alkaline solution (pH 8–14) should be added and it should be stirred at 10°–60° C. for 30 minutes-10 hours.

Specific examples of the alkaline solution include a solution containing at least one of sodium hydroxide, potassium hydroxide, ammonium hydroxide, sodium bicarbonate, sodium carbonate, ammonia, etc. and known methods of extraction such as hot water extraction may be used. Isolation of the extraction solution may be carried out by known methods such as filtration, decantation, centrifugation, etc.

Besides water, ethanol, acetone, etc. may be used as extraction solvents and the residue of the solvent may be freeze-dried, spray-dried, etc. in the usual way.

The effective components of the extract may be mixed with a suitable pharmaceutically acceptable carrier such as an excipient, a binding agent, a diluent, and used in the form of, for example, granules, powder, hard capsules, soft capsules, an ointment, a syrup, suppositories, an injection; in any oral or non-oral form, and also may be mixed and used directly in solutions, powders, granules, tablets, emulsions, jellies, etc. or any other form, or used alone in a form as described above, or as a concentrated substance; or alternatively it may be consumed by mixing with foods or beverages.

The dosage depends on the kind of ailment, and the extent of the condition of the patient, but when in a liquid form 2 ml–500 ml per day of 1–1000 mg/liter solution should be taken, and when the extraction is in a powder form, 0.2 mg–5 g per day should be taken.

*Aspalathus linearis* alkaline extracts were subjected to an acute toxicity test with rats and mice. There were no mortalities, no abnormal behaviour in the animals was observed and there were no abnormal values on biochemical examination of blood and pathological examination of tissues.

EFFECT

The present invention is an anti-viral, anti-cancer, anti-bacterial, sterilizing agent, and according to the present invention one can obtain extracts which prevent infection and suppress replication of various viruses such as influenza virus, herpes simplex virus, rotavirus, and hepatitis virus, and retroviruses such as adult T-cell leukemia, or HIV (human immunodeficiency virus), and the growth or proliferation of micro-organisms such as bacteria, mold etc., and moreover prevent, improve and/or cure malignant tumors without side-effects.

The present invention will now be described by the following non-limiting Examples. In the following Examples, "%" means "weight %".

EXAMPLES

Production Example 1

The leaves and stems of *Aspalathus linearis* were cut into 5 mm lengths, and the processes of rolling, enzyme fermentation, drying in the sun, were carried out to produce the dried leaves. 3 g of these dried leaves were extracted in 100 ml of 85° C. hot water for 3 hours and then the leaves and stems were dried indoors. 50 ml of 1% sodium hydroxide was added to the dried leaves obtained and this was shaken vigorously at 45° C. for 3 hours, then filtered through sanitary cotton (0.5 cm) thick), and the extract containing various acid polysaccharides was obtained. The extraction solution thus obtained was dried to a powder which contained 16% reducing sugars and 20% neutral sugars.

Production Example 2

The dried powder of the extract was obtained in the same way as in Production Example 1 using 2% ammonium hydroxide for the alkaline solution instead of 1% sodium hydroxide. The dried powder contained 14% reducing sugars and 21% neutral sugars.

Production Example 3

The dried powder of the extract was obtained in the same way as in Production Example 1 using 1% sodium carbonate for the alkaline solution instead of 1% sodium hydroxide and one layer of gauze for filtration instead of sanitary cotton. The dried powder contained 18% reducing sugars and 29% neutral sugars.

Production Example 4

The leaves and stems of *Aspalathus linearis* were cut into 5 mm lengths, and the processes of rolling, enzyme fermentation, drying under the sun were carried out to produce the dried leaves. 50 ml of 1% sodium hydroxide was added to 3 g of the dried leaves obtained and this was shaken vigorously at 45° C. for 3 hours, then filtered through sanitary cotton (0.5 cm thick) and the extract containing various acid polysaccharides was obtained. The extraction solution thus obtained was dried to a powder which contained 22% reducing sugars and 37% neutral sugars.

Production Example 5

The leaves and stems of *Aspalathus linearis* were cut into 5 mm lengths, and the processes of rolling, enzyme fermentation, drying under the sun were carried out to produce the dried leaves. 3.5 g of the dried leaves were extracted in 500 ml of 85° C. hot water for 3 hours, then the above leaves with stems were dried inside. The dried leaves were shaken vigorously in 50 ml of 1% potassium hydroxide at 45° C. for 3 hours, then filtered through two layers of gauze and the extraction solution containing acid polysaccharides was obtained. The extraction solution thus obtained was freeze-dried, and the powder contained 22% reducing sugars, 30% neutral sugars, and 17% uronic acid.

Production Example 6

The leaves and stems of *Aspalathus linearis* were cut into 5 mm lengths, and the processes of rolling, enzyme fermentation, drying under the sun were carried out to produce the dried leaves. 3 g of the dried leaf were extracted in 100 ml of 85° C. hot water for 3 hours, then the above leaves with stems were dried inside. The dried leaves were shaken vigorously in 50 ml of sodium hydroxide at 45° C. for 3 hours, then filtered through sanitary cotton (0.5 cm thick) to obtain the extract. The said extract was freeze-dried and the dried powder thus obtained was was used as the crude extract of *Aspalathus linearis*. The said crude extract was dissolved in distilled water, then ethanol was added and precipitated substances between 25%–75% ethanol concentration were centrifuged at 3000 rpm for 20 minutes, and the precipitate thus obtained was dried to obtain the purified acid polysaccharides. The dried powder of acid polysaccharides contained 22.5% uronic acids, 50.5% neutral sugars, and 26.5% reducing sugars.

Production Example 7

The dried powder of the extract (crude extract) was obtained in the same way as in Production Example 6. The acid crude extract was dissolved in distilled water, and precipitated substances with the addition of ethanol between 25%–75% concentration were obtained by centrifugation at 3000 rpm for 20 minutes, and the precipitate was dried and designated as the purified acid polysaccharides. The final supernatant of 75% ethanol precipitation was concentrated, dried and designated as 75-sup. The dried powder of acid polysaccharides contained 22% uronic acids, 48% neutral sugars and 25% reducing sugars.

Practical Example 1

The dried powder obtained in Production Example 1 was applied to cultured MDCK cells or to MA104 cells. Immediately after the application, MDCK was infected with influenza virus and MA104 was infected with herpes simplex virus, cultured spontaneously with the dried powder and the plaque formation was observed. Results showed that the plaque by influenza virus was inhibited completely (100%) by 0.1 mg/ml, and in the case of the herpes virus plaque formation was inhibited more than 90% by 1 $\mu$g/ml of the said dried powder (the said extract).

Practical Example 2

MT-4 cells ($2.5 \times 10^4$ cells/well) were infected with HIV-$1_{IIIB}$ and immediately after infection, the infected cells were spread over a microtiter plate with 96 wells containing various concentrations of the said purified extract obtained in Production Example 1, and cultured in a $CO_2$ incubator at 37° C. for 5 days. The number of viable cells was measured by MTT methods. The anti-HIV activity was expressed as the concentration which showed 50% protection against HIV-induced cytopathogenicity by test substances ($EC_{50}$; 50% effective concentration). The $EC_{50}$ was less than 21 $\mu$g/ml.

Practical Example 3

MT-4 cells ($2.5 \times 10^4$ cells/well) were infected with HIV-$1_{IIIB}$, and immediately after infection, the infected cells were spread over a microtiter plate with 96 wells containing various concentrations of the said purified extract obtained in Production Example 2, and cultured in a $CO_2$ incubator at 37° C. for 5 days. The number of viable cells was measured by MTT methods. The anti-HIV activity was expressed as the concentration which showed 50% protection against HIV-induced cytopathogenicity by test substances ($EC_{50}$; 50% effective concentration). The $EC_{50}$ was less than 48 $\mu$g/ml.

Practical Example 4

MT-4 cells ($2.5 \times 10^4$ cells/well) were infected with HIV-$1_{IIIB}$ and immediately after infection, the infected cells were spread over a microtiter plate with 96 wells containing various concentrations of the said purified extract obtained in Production Example 3, and cultured in a $CO_2$ incubator at 37° C. for 5 days. The number of viable cells was measured by MTT methods. The anti-HIV activity was expressed as the concentration which showed 50% protection against HIV-induced cytopathogenicity by test substances ($EC_{50}$; 50% effective concentration). The $EC_{50}$ was less than 21 $\mu$g/ml.

Practical Example 5

The said extract obtained in Production Example 4 was applied to cultured MDCK cells or to MA104 cells, MDCK cells were infected with the influenza virus and MA104 cells were infected with herpes simplex virus then cultured spontaneously with the dried powder, and plaque formation was observed. The plaque formation by influenza virus was inhibited almost 100% by 0.15 mg/ml, and in the case of herpes simplex virus, plaque formation was inhibited more than 90% by 3 $\mu$g/ml of the said extract.

Practical Example 6

MT-4 cells ($2.5 \times 10^4$ cells/well) were infected with HIV-$1_{IIIB}$, and immediately after infection, the infected cells were spread over a microtiter plate with 96 wells containing various concentrations of the said purified extract obtained in Production Example 6, and cultured in a $CO_2$ incubator at 37° C. for 5 days. The number of viable cells was measured by MTT methods. The anti-HIV activity of acid polysaccharides was expressed as the concentration which showed 50% protection against HIV-induced cytopathogenicity by test substances ($EC_{50}$; 50% effective concentration). The $EC_{50}$ of the said acid polysaccharides was 15 $\mu$g/ml.

Practical Example 7

NUGC-4 ($1 \times 10^6$ cells/ml) derived from stomach cancer were injected subcutaneously to 20 mice. From the following day, as the experimental group 10 of these mice were injected (i.p.) daily with 1000 mg/ml of the said extract obtained in Production Example 1. Mice which were not administered with the said extract were used as the control group. Growth of cells was calculated 3 weeks after administration of the said extract. Numbers of cells in the control group markedly increased while an increase of tumor cells in the experimental group was remarkably inhibited.

Practical Example 8

NUGC-4 ($1 \times 10^6$ cells/ml) derived from stomach cancer were injected subcutaneously to 20 mice. From the following day, as the experimental group 10 of these mice were injected (i.p.) daily with 500 $\mu$g/ml of the said extract obtained in Production Example 5. Mice which were not administered with the said extract were used as the control group. Growth of cells was calculated 1 month after administration of the said extract. After 1 month the cells in the control group had markedly increased, there were some areas of necrosis, and some animals died. In the experimental groups however, the number of cells was remarkably inhibited, and no animals died.

Practical Example 9

NUGC-4 ($1 \times 10^6$ cells/ml) derived from stomach cancer were put into a 96-well microtiter plate containing various concentrations of the 75-sup fraction obtained in Production Example 7, and cultured in a $CO_2$ incubator at 37° C. for 5 days. The number of viable cells was measured by MTT methods. The anti-cancer activity of acid polysaccharides was expressed as the concentration which inhibited 50% growth of tumor cells ($IC_{50}$; 50% effective concentration). The $IC_{50}$ of the 75-sup fraction was 200 $\mu$g/ml, but purified acid polysaccharides (25–75% precipitated fraction) showed no suppresion of tumor cell growth.

It will be appreciated that the instant specification is set forth by way of illustration and not limitation and that various modifications and changes can be made without departure from the spirit and scope of the present invention.

What is claimed is:

1. An anti-viral, anti-bacterial and anti-cancer composition comprising an anti-viral, anti-bacterial or anti-cancer effective amount of an alkaline extract of *Aspalathus linearis* as an active component together with a pharmaceutically acceptable carrier, wherein the extract is obtained by contacting water at a temperature of 70° to 100° C. with leaves, stems or roots of *Aspalathus linearis* and drying the leaves, stems or roots and then contacting the dried leaves, stems or roots with a solution containing at least one alkaline compound.

2. The anti-viral, anti-bacterial and anti-cancer composition of claim 1, wherein the extract is obtained by contacting water at a temperature of 70° to 100° C. with leaves, stems or roots of *Aspalathus linearis* and drying the leaves, stems or roots and then contacting the dried leaves, stems or roots with a solution containing at least one alkaline compound.

3. The anti-viral, anti-bacterial and anti-cancer composition of claim 1, wherein the alkaline extract is obtained by contact of leaves, stems or roots of *Aspalathus linearis* with an alkaline solution containing at least one alkaline compound selected from the group consisting of sodium carbonate, sodium bicarbonate, potassium hydroxide, sodium hydroxide, ammonium hydroxide and ammonia.

4. The anti-viral, anti-bacterial and anti-cancer composition of claim 1, wherein the at least one alkaline compound is selected from the group consisting of sodium carbonate, sodium bicarbonate, potassium hydroxide, sodium hydroxide, ammonium hydroxide and ammonia.

5. A method of producing an anti-viral, anti-bacterial and anti-cancer agent comprising (a) contacting at least one of leaves, stems or roots of *Aspalathus linearis* with water at a temperature of 70° to 100° C., (b) drying the leaves, stems or roots, (c) contacting the dried leaves, stems or roots from step (b) with a solution containing at least one alkaline compound selected from the group consisting of sodium carbonate, sodium bicarbonate, potassium hydroxide, sodium hydroxide, ammonium hydroxide and ammonia to produce an extract, and (d) isolating said extract from step (c) by filtration.

* * * * *